US008961676B2

(12) United States Patent
Hydrick

(10) Patent No.: US 8,961,676 B2
(45) Date of Patent: Feb. 24, 2015

(54) BIOCOMPATIBLE ADHESIVE FOR ATTACHING ORNAMENTAL ACCESSORIES

(71) Applicant: Katie Clark Hydrick, Provo, UT (US)

(72) Inventor: Katie Clark Hydrick, Provo, UT (US)

(73) Assignee: Girlie Glue, L.L.C., Provo, UT (US)

( * ) Notice: Subject to any disclaimer, the term of this patent is extended or adjusted under 35 U.S.C. 154(b) by 0 days.

(21) Appl. No.: 13/959,558

(22) Filed: Aug. 5, 2013

(65) Prior Publication Data

US 2014/0083611 A1 Mar. 27, 2014

Related U.S. Application Data

(60) Provisional application No. 61/744,469, filed on Sep. 27, 2012, provisional application No. 61/793,622, filed on Mar. 15, 2013.

(51) Int. Cl.
*C09J 5/00* (2006.01)
*A61K 8/60* (2006.01)
*C09J 105/00* (2006.01)
*A44C 15/00* (2006.01)

(52) U.S. Cl.
CPC *C09J 105/00* (2013.01); *C09J 5/00* (2013.01); *A44C 15/0005* (2013.01); *A61K 2800/5922* (2013.01); *A61K 8/60* (2013.01); *C09J 2405/00* (2013.01); *C09J 2499/00* (2013.01)
USPC ........................................ 106/162.1; 514/777

(58) Field of Classification Search
USPC ................. 106/162.1; 426/639, 660; 514/777
See application file for complete search history.

(56) References Cited

U.S. PATENT DOCUMENTS

2008/0121557 A1 5/2008 Jacobsen
2012/0207884 A1 8/2012 Adams et al.
2013/0309369 A1* 11/2013 Hershberg .................... 426/103

OTHER PUBLICATIONS

"Nectar", definitions downloaded from MyDictionary.com Jul. 14, 2014.*
"Syrup", definitons downloaded form MyDictionary.com Jul. 14, 2014.*
Zelman, "The Truth About Agave", www.webmd.com/diet/features/the-truth-about-agave, downloaded Jul. 14, 2014.*
Baldy Baby Bows L.L.C., full website, www.baldybabybows.com/id47, at least as early as Mar. 4, 2013, 7 pages.
The Bear and the Blackberry, "Amylia's Monkey Cake," May 9, 2012, retrieved Jan. 29, 2014, from http://thebearandtheblackberry.wordpress.com/ tag/peanut-butter-and-bananas-are-in-love-forever-and-agave-syrup-is-the-glue-that-holds-them-together/, 7 pages.
Jaworski, "Ingredient Substitution Table," www.joyofbaking.com, retrieved via Internet Wayback Machine Archive for Apr. 27, 2003, on Jan. 31, 2014 (https://web.archive.org/web/20030427194428/http://joyofbaking.com/IngredientSubstitution.html), 9 pages.

(Continued)

*Primary Examiner* — David M Brunsman
(74) *Attorney, Agent, or Firm* — Clayton, Howarth & Cannon, P.C.

(57) ABSTRACT

A non-toxic, biodegradable, and water soluble adhesive made from a reduction of all natural substances. The adhesive is suited for gluing ornamental accessories to infants, children, young adults, adults or pets. The adhesive is further suited for temporarily attaching items to surfaces. The adhesive may comprise a reduction of a mixture comprising a syrup, a nectar, and a refined sugar.

6 Claims, 3 Drawing Sheets

(56) References Cited

OTHER PUBLICATIONS

Lunch in a Box: Building a Better Bento, "Edible glue: How to anchor food decorations," www.lunchinabox.net, retrieved via Internet Wayback Machine Archive for Jan. 5, 2011, on Jan. 22, 2014 (https://web.archive.org/ web/20110105042932/http:/lunchinabox.net/2008/10/29/edible-glue-how-to-anchor-food-decorations), 11 pages.

O.Berk Company, LLC, "News Stories—Squeeze With Ease . . . Totally Tubular," www.oberk.com, retrieved via Internet Wayback Machine Archive for Nov. 28, 2011, on Jan. 23, 2014 (https://web.archive.org/web/20111128013749/ http://www.oberk.com/news-events/news-stories-squeeze-with-ease.html), 4 pages.

Rae, "Tips for Substituting Agave in Baked Goods," www.thekitchn.com, retrieved via Internet Wayback Machine archive for Mar. 2, 2012, on Jan. 31, 2014 (https://web.archive.org/web/20120302134030/http://www.thekitchn.com/5-tips-on-substituting-agave-i-105651), 2 pages.

Wise Geek, "How Do I Make Wheat Paste?" www.wisegeek.com, retrieved via Internet Wayback Machine Archive for Aug. 6, 2012, on Jan. 23, 2014 (https://web.archive.org/web/20120806141343/http://www.wisegeek.com/how-do-i-make-wheat-paste.htm), 3 pages.

\* cited by examiner

BIOCOMPATIBLE ADHESIVE FOR ATTACHING ORNAMENTAL ACCESSORIES

CROSS-REFERENCE TO RELATED APPLICATIONS

This application claims the benefit of U.S. Provisional Application Nos. 61/744,469 and 61/793,622, filed Sep. 27, 2012 and Mar. 15, 2013, respectively, which are hereby incorporated by reference herein in entirety, including but not limited to those portions that specifically appear hereinafter, the incorporation by reference being made with the following exception: In the event that any portion of the above-referenced provisional applications are inconsistent with this application, this application supercedes said above-referenced provisional application.

STATEMENT REGARDING FEDERALLY SPONSORED RESEARCH OR DEVELOPMENT

Not Applicable.

BACKGROUND

1. The Field of the Present Disclosure

The present disclosure relates generally to adhesives, and more particularly, but not necessarily entirely, to non-toxic adhesives for use in attaching ornamental accessories to living organisms, including humans and animals.

2. Description of Background Art

Personal appearance of living organisms, particularly humans and domesticated animals kept as pets, can be enhanced by attaching ornamental accessories such as hair bows, ribbons, earrings, and the like. On adults such ornamental accessories can often be added by using, for example, a hair clip integrated into the ornamental accessory. However, hair clips typically cannot be used on infants or small children due to the lack of hair. Some attempts have been made to provide adhesives materials for attaching accessories to infants and small children.

U.S. Patent Publication No. 2008/0121557 (published May 29, 2008 to Jacobsen) discloses a hair bow kit for infants and children comprising a supply of liquid adhesive and a plurality of infant hair bows. Jacobsen discloses three suitable adhesives for use in its kit, including: (1) a composition of polyvinyl acetate emulsion, phthalate ester, and vinyl polymer; (2) a commercially available adhesive sold under the tradename "IT STAYS!"; and (3) a commercially available adhesive sold under the tradename "BODY GLUE" formed of a composition of water, panthenol, PVP, polyvinyl alcohol, methylparaben, diazolidinyl urea. While Jacobsen claims that the above adhesives are non-toxic, Jacobsen's adhesives are non-natural and parents may be reluctant to apply chemicals with scary-sounding names to the heads of new born infants.

Parents, having concerns over commercially available adhesives, have tried using home solutions with more natural substances to attach accessories. For example, in the past, parents have attached bows to the head of infants by placing a dab of corn syrup on the underside of the bow and then firmly pressing the bow to the desired location. Corn syrup, however, has been found to be only suitable for small accessories. That is, experience has shown that corn syrup is unsuitable for holding large accessories in place for any extended amount of time due to the relatively weak bonding strength. Further, corn syrup is difficult to transport for personal use as it is only sold in bulky containers.

Despite the advantages of known adhesives, improvements are still being sought. For example, it would be an improvement to provide an all natural adhesive with superior holding characteristics as compared to the prior art. The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
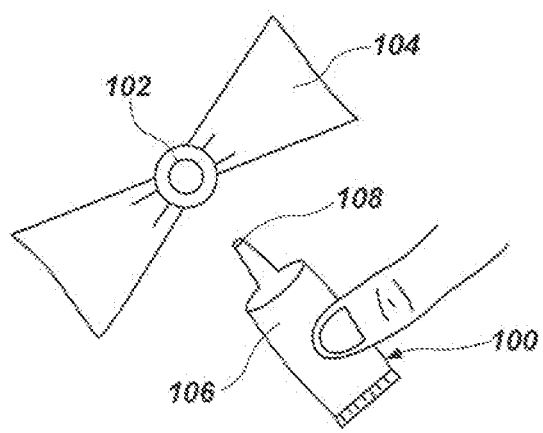
FIG. 1 is a view of a squeeze tube dispenser used to apply a dab of adhesive to secure ornamental accessory to a living organism according to an embodiment of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

In describing and claiming the present disclosure, the following terminology will be used in accordance with the definitions set out below. As used in this specification and the appended claims, the singular forms "a," "an," and "the" include plural referents unless the context clearly dictates otherwise. As used in this specification and the appended claims, the terms "comprising," "having," "including," "containing," "characterized by," and grammatical equivalents thereof are inclusive or open-ended terms that do not exclude additional, unrecited elements or method steps. As used in this specification and the appended claims, the term "about,"

when used to modify a numerical value, means within 20% of the numerical value (either higher or lower).

As used in this specification and the appended claims, the terms "accessory" or "accessories" should be construed broadly, and refers to any object that may be used for ornamental or non-ornamental purposes, such as bows, ribbons, earrings, flowers, yarn, fabric, string, felt, real hair, fake flowers, fake hair, fake mustaches, fake eyebrows, jewelry, pet accessories, costume jewelry, clothing, hats, head bands, and the like.

An objective of the present disclosure is to provide an adhesive with all natural ingredients for use in attaching items, such as ornamental accessories, to surfaces, such as skin. It will be appreciated that the present disclosure may be used in a wide variety of situations, including attaching items to any type of surface, including skin, earlobes, hair, fur, and clothing. The items attached using the adhesive may include all types of accessories, whether ornamental or non-ornamental.

An objective of the present disclosure is to provide an adhesive with sufficient viscosity that it does not drop or run.

An objective of the present disclosure is to provide an adhesive that requires little or no drying time.

An objective of the present disclosure is to provide a water soluble adhesive that easily washes off with water.

An objective of the present disclosure is to provide a non-toxic adhesive made from all natural ingredients.

An objective of the present disclosure is to provide a method of manufacturing an adhesive for use in attaching items, such as ornamental accessories, to all types of surfaces.

An objective of the present disclosure is to provide an improved method of applying ornamental accessories to infants, children, young adults, adults and pets.

An objective of the present disclosure is to provide an improved adhesive dispenser.

An objective of the present disclosure is to provide an improved method of making an adhesive according to an embodiment of the present disclosure.

Referring now to FIG. 1, there is depicted an adhesive dispenser 100 shown applying a dab 102 of adhesive to an accessory 104 according to an embodiment of the present disclosure. The dispenser 100 may include a squeezable tube 106 having an orifice 108. In an embodiment, the orifice 108 is between 2 millimeters to 4 millimeters, or about 3 millimeters. It will be appreciated that the orifice 108 may be larger or smaller. In an embodiment, the orifice 108 may be flat or a needle-type orifice. In an embodiment, the orifice 108 may be sealed with a cap or flip-top.

Figure 2:
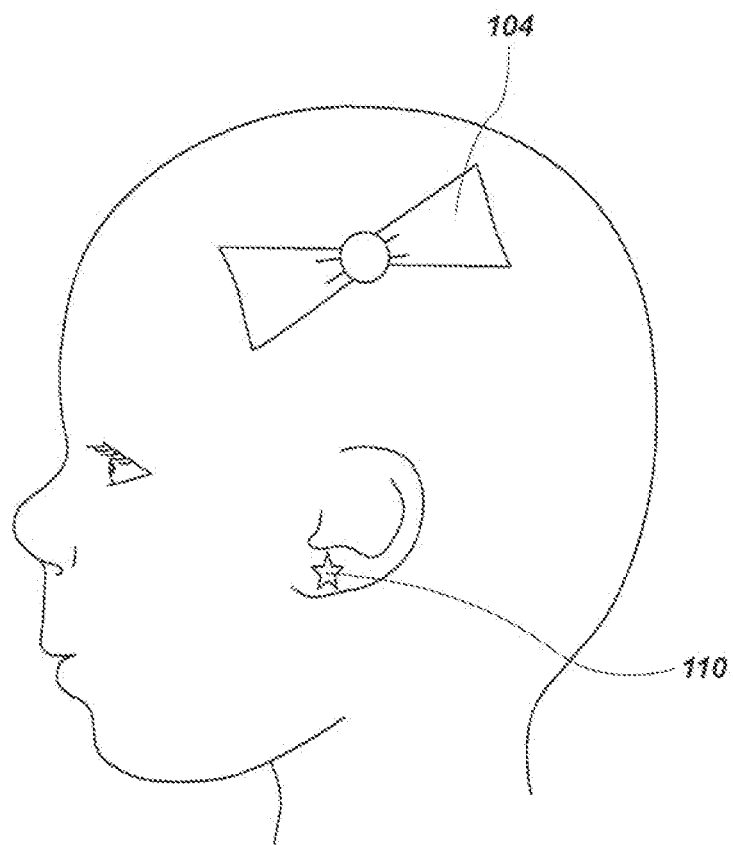
FIG. 2 is a side view of an infant's head having ornamental accessories attached thereto using an adhesive according to an embodiment of the present disclosure.

Referring now to FIG. 2, there is depicted the accessory 104 secured to an infant's head using an adhesive according to an embodiment of the present disclosure. In particular, the accessory 104, coated with a dab of the adhesive, is gently pressed against the infant's head until it sticks. Also shown is an accessory 110 attached to the infant's earlobe. It will be appreciated that the use of the infant in FIG. 2 to describe the present invention should not be considered limiting on the scope of the present disclosure. Indeed, the adhesive of the present invention may be utilized on infants, children, young adults, adults, and pets. The adhesive may also be used on inanimate objects according to an embodiment of the present disclosure.

Figure 3:
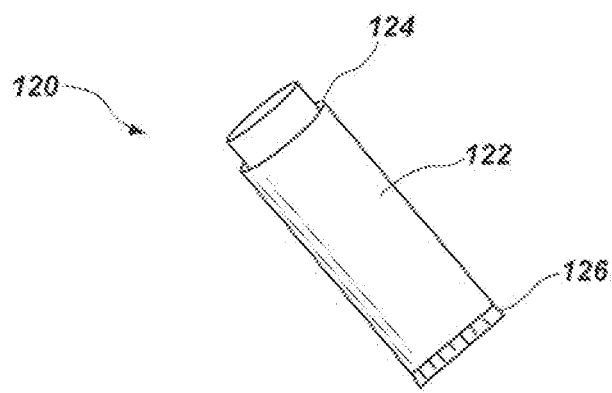
FIG. 3 is a view of a glue-stick type dispenser for an adhesive according to an embodiment of the present disclosure.

Referring now to FIG. 3, there is depicted an adhesive dispenser 120 according to an embodiment of the present disclosure. The dispenser 120 may include a tubular body member 122 having an orifice 124 at one end and a head 126 attached to a threaded shaft (not visible). The adhesive may be dispensed from the orifice 124 when a user twists the head 126. In particular, turning the head 126 will turn the threaded shaft which pushes the adhesive out of the orifice 124.

Figure 4:
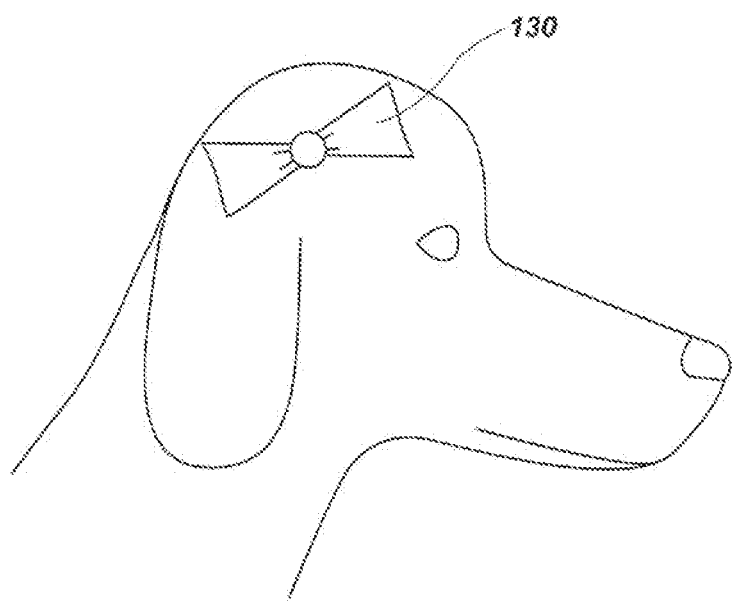
FIG. 4 is a side view of a pet's head having an ornamental accessory attached thereto using an adhesive according to the present disclosure.

Referring now to FIG. 4, there is depicted an accessory 130 attached to a pet using an adhesive according to the present disclosure.

It will be appreciated that the adhesive of the present disclosure may be utilized to temporarily stick any small object to almost any surface. The size of the accessory may dictate the amount of adhesive to utilize. Adhesion occurs when the object, coated with a dab of adhesive, is gently pressed against the desired surface. To remove the object, the object is peeled back from the surface. If there is any resistance to removal, water may be applied to dissolve the adhesive. The adhesive is non-toxic so it is completely harmless if ingested, although ingestion is not recommended.

Figure 5:
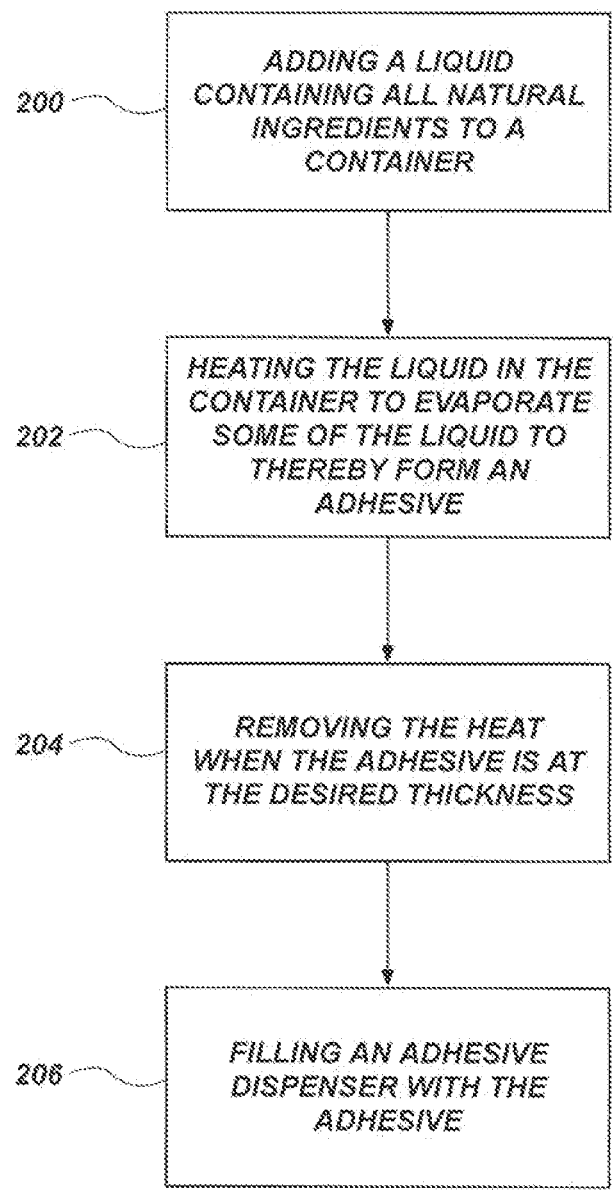
FIG. 5 is a flow chart of an exemplary method of forming an adhesive according to an embodiment of the present disclosure.

Referring now to FIG. 5, there is depicted a flow chart of a method for making adhesive according to an embodiment of the present disclosure. At step 200, a liquid containing all natural ingredients is added to a container. The all natural ingredients may include nectar, Agave nectar, refined sugar, granulated sugar, white sugar, brown sugar, syrup, corn syrup, molasses, honey, and sugars. The liquid with all natural ingredients may comprise two or more of a syrup, a nectar, and a refined sugar. The liquid with all natural ingredients may comprise a syrup, a nectar, and a refined sugar. In an embodiment, the ratio of the syrup, the nectar, and the refined sugar is about 16:1:2. In an embodiment, the syrup is one of corn syrup and maple syrup, the nectar is Agave nectar, and the refined sugar is one of white sugar and brown sugar.

In an embodiment, the composition used to form an adhesive according to an embodiment of the present disclosure is pursuant to any one of the Formulas 1-10 shown in Table 1, below.

TABLE 1

|  | Formula 1 | Formula 2 | Formula 3 | Formula 4 | Formula 5 | Formula 6 | Formula 7 | Formula 8 | Formula 9 | Formula 10 |
|---|---|---|---|---|---|---|---|---|---|---|
| Agave Nectar | 1 part |  | 1 part | 1 part |  | 1 part |  | 8 parts | 4 parts |  |
| Corn Syrup | 4 parts | 16 parts | 8 parts | 16 parts | 16 parts | 16 parts | 8 parts |  |  | 8 parts |
| White Granulated Cane Sugar | ½ part | 1 part |  |  | 1 part | 2 parts | 1 part | 1 part |  |  |
| Brown Sugar | ½ part |  |  | 1 part |  |  |  |  | 1 part | 1 part |
| Maple Syrup | 1 part |  | 1 part |  |  |  | 1 part |  | 4 parts | 1 part |
| Molasses |  | 1 part |  |  |  |  |  |  |  |  |

TABLE 1-continued

| | Formula 1 | Formula 2 | Formula 3 | Formula 4 | Formula 5 | Formula 6 | Formula 7 | Formula 8 | Formula 9 | Formula 10 |
|---|---|---|---|---|---|---|---|---|---|---|
| Results | When heated to the correct degrees, works well. Slightly darker in color and has more of a scent. | Works well when heated to the correct degrees. Darker color and stronger, more unpleasant scent. | Not quite as thick as desired when a solid sugar is not added. | When heated to the correct degrees, works well. Slightly darker in color and has more of a scent. | Works well when heated to the correct degrees, just lacks a scent. | Works great. Nice, light color. Nice, very light scent. This is the preferred combination. | Works well when heated to the correct degrees, just has a slightly stronger scent. | When heated to the correct degrees, works well. Slightly darker in color and has more of a scent. | When heated to the correct degrees, works well. Slightly darker in color and has more of a scent. | When heated to the correct degrees, works well. Slightly darker in color and has more of a scent. |

All formulas were tried at various temperatures, but found that a good range of temperatures is 224-226 degrees. Each batch was mixed in a large pan over the stove and stirred regularly until the mixture reached the desired temperature range of 224-226 degrees. The time varied with the ingredients and the amount of mixture - anywhere from 20-45 minutes. The mixtures were then cooled to room temperature and tested for thickness, color and scent.

At step 202, the liquid in the container is heated to evaporate excess water to form a reduction ion of the liquid that is the adhesive. The liquid may be brought to boiling and maintained at a temperature between boiling point or 230 degrees. In an embodiment, the liquid may be maintained at 225 degrees. In an embodiment, the temperature may fall within the ranges indicated in Table 2, below.

TABLE 2

| | 221° or below | 222°-223° | 224°-225° | 226° | 227° or above |
|---|---|---|---|---|---|
| Combination of Natural Sugars and Syrups | The combination of ingredients heated to this temperature creates a thin syrup. | The combination of ingredients heated to this temperature creates a slightly thicker syrup. | The combination of ingredients heated to this temperature creates a very thick but still fluid syrup that is a good consistency to act as an adhesive. | The combination of ingredients heated to this temperature creates a very thick syrup that is sticky. | The combination of ingredients heated to this temperature is very thick. |

Preparation Parameters - The ingredients were mixed in a large pot, stirred regularly and boiled continuously until they reached the desired temperature range of 224-225. At this point the adhesive mixture is taken off the heat and allowed to cool to room temperature. At room temperature the mixture is the desired thickness and consistency to act as an adhesive.

At step 204, the heat is removed when the adhesive is at the desired thickness and viscosity. Ideally, the adhesive should not be too thin or too thick. At step 206, an adhesive dispenser is filled with the adhesive.

Those having ordinary skill in the relevant art will appreciate the advantages provide by the features of the present disclosure. For example, it is a feature of the present disclosure to provide an adhesive for use in attaching ornamental accessories to skin. Another feature of the present disclosure to provide such an adhesive with non-toxic and natural substances. It is a further feature of the present disclosure, in accordance with one aspect thereof, to provide a convenient dispenser for the adhesive.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of forming an adhesive:
    combining a nectar and a syrup to form a mixture, wherein the nectar is Agave nectar and wherein the syrup is corn syrup;
    combining granulated white sugar to the mixture such that ratio of Agave nectar to corn syrup to granulated white sugar is about 1:16:2;
    forming the adhesive by heating the mixture in the range from about 220 degrees to about 230 degrees to remove excess water;

cooling the adhesive, to create a very thick but still fluid syrup that is a good consistency to act as an adhesive; and filling an adhesive dispenser with the adhesive.

2. The method of claim 1, further comprising heating the mixture to between 224 degrees to 225 degrees.

3. The method of claim 1, further comprising heating the mixture to between 224 degrees and 226 degrees.

4. The method of claim 1, wherein the adhesive dispenser comprises a squeeze tube having an orifice of about 3 to 4 millimeters.

5. A method of applying an ornamental accessory to a surface:

placing a dab of adhesive on a portion of the ornamental accessory; and pressing the dabbed portion of ornamental accessory to surface;

wherein the adhesive is derived from a reduction of a mixture, the mixture obtained from carrying out the steps of:

combining a nectar and a syrup to form a mixture, wherein the nectar is Agave nectar and wherein the syrup is corn syrup;

combining granulated white sugar to the mixture such that ratio of Agave nectar to corn syrup to granulated white sugar is about 1:16:2;

forming the adhesive by heating the mixture in the range from about 220 degrees to about 230 degrees to remove excess water;

cooling the adhesive, to create a very thick but still fluid syrup that is a good consistency to act as an adhesive; and filling an adhesive dispenser with the adhesive.

6. An adhesive comprising a reduction of a mixture comprising a syrup, a nectar, and a refined sugar wherein the nectar is Agave nectar and the syrup is corn syrup and the refined sugar is a white granulated sugar and wherein the ratio of Agave nectar to corn syrup to granulated white sugar is about 1:16:2, wherein the reduction of the mixture comprise the steps of heating the mixture to a temperature in the range from about 220 degrees to about 230 degrees to remove excess water and cooling the mixture to create a very thick but still fluid syrup that is a good consistency to act as an adhesive.

* * * * *